United States Patent [19]

Gasser et al.

[11] Patent Number: 5,224,957

[45] Date of Patent: Jul. 6, 1993

[54] METHOD OF PROVIDING A COMPOSITION FOR AN EYE

[75] Inventors: Oswald Gasser; Erich Wanek, both of Seefeld; Rainer Guggenberger, Herrsching; Klaus-Peter Stefan, Seefeld; Klaus Ellrich, Wörthsee, all of Fed. Rep. of Germany

[73] Assignees: THERA Patent GmbH & Co.; KG Gesellschaft für industrielle Schutzrechte, Seefeld, Fed. Rep. of Germany

[21] Appl. No.: 571,303

[22] Filed: Aug. 22, 1990

[30] Foreign Application Priority Data

Aug. 22, 1989 [DE] Fed. Rep. of Germany ....... 3927667

[51] Int. Cl.$^5$ .............................................. A61F 2/16
[52] U.S. Cl. ........................................ 623/6; 604/290; 128/898; 606/107; 522/186
[58] Field of Search ............... 623/4, 6; 604/289, 290; 128/898; 351/160 R, 160 H; 606/107; 522/186, 181, 182, 90, 75

[56] References Cited

U.S. PATENT DOCUMENTS

| | | | |
|---|---|---|---|
| 4,542,542 | 9/1985 | Wright | 623/6 |
| 4,543,398 | 9/1985 | Bany et al. | 525/474 |
| 4,608,050 | 8/1986 | Wright et al. | 623/6 |
| 4,638,040 | 1/1987 | Hammar et al. | 526/245 |
| 4,673,539 | 6/1987 | Hammar et al. | 264/1.1 |
| 4,997,441 | 3/1991 | Sulc et al. | 623/6 |
| 5,008,102 | 4/1991 | York | 424/59 |
| 5,011,275 | 4/1991 | Mueller | 351/160 H |
| 5,015,254 | 5/1991 | Greite | 623/6 |
| 5,035,710 | 7/1991 | Nakada et al. | 623/6 |
| 5,133,745 | 7/1992 | Falcetta et al. | 623/6 |

FOREIGN PATENT DOCUMENTS

| | | | |
|---|---|---|---|
| 0308130 | 3/1989 | European Pat. Off. | |
| 1103861 | 7/1984 | U.S.S.R. | 604/289 |
| 1503802 | 8/1989 | U.S.S.R. | 128/898 |
| 8900029 | 1/1989 | World Int. Prop. O. | 606/107 |

OTHER PUBLICATIONS

CA 108:39690y Comparison of Photostabilization in acrylic/urethane and acrylic/melamine coatings containing hindered amines and ultraviolet absorbers.

CA 114:171360y Polymer compositions for interacular lenses.

CA 114:230037a Difunctional (meth)acrylate compounds, manufacture, and uses.

*Primary Examiner*—C. Fred Rosenbaum
*Assistant Examiner*—Mark O. Polutta
*Attorney, Agent, or Firm*—Robert W. Becker & Associates

[57] ABSTRACT

A method is provided for treating cataracts and other eye diseases, and includes the use of photopolymerizable compositions for preparing an intraocular-lens filling material which is used during an operation with an inserted intraocular-lens shell. The photopolymerizable compositions contain the following components:

a) 90–99.99% by weight, preferably 94–99.799% by weight of at least one at least difunctional acrylic and/or methacrylic acid ester, b) 0.01–5% by weight, preferably 0.1–2% by weight, of at least one photoinitiator which is activatable with light in the wavelength range 400–500 nm, c) 0–9.98% by weight, preferably 0.001–2% by weight, of a UV-absorber which can absorb light of wavelengths <400 nm, and d) 0–9.98% by weight, preferably 0.1–2% by weight, of other auxiliary substances, such as dyes or activators for the photoinitiator, for example tertiary amines, the quantity particulars referring in each case to the total mass.

13 Claims, No Drawings

METHOD OF PROVIDING A COMPOSITION FOR AN EYE

BACKGROUND OF THE INVENTION

The present invention relates to the use of photopolymerizable compositions for preparing an intraocular-lens filling material which is used during an operation where an intraocular lens shell is inserted. The treatment of cataracts (grey cataract) and other eye complaints frequently requires removal of the natural lens of the eye. Since the implantation of the first artificial intraocular lens (IOL) of polymethylmethacrylate (PMMA) (H. Ridley, 1948), this operation has become routine in many ophthalmological clinics.

Depending upon the location of insertion, a distinction is made between three IOL types: Anterior chamber lenses, intrapupillary lenses and posterior chamber lenses. The lenses consist of a lens body and a haptic which ensures the fixing of the lens. The lens body is usually made from PMMA homopolymers, more rarely from copolymers such as PMMA-ethylene glycol dimethacrylate, PMMA-hydroxyethyl methacrylate (HEMA) or PMMA-vinyl pyrrolidone, and in more recent times from silicone elastomers. In many cases a UV absorber is added to protect the retina from UV light, as is also done by the natural lens. The haptic may be very differently shaped and usually consists of polypropylene, more rarely known of PMMA.

A disadvantage common to all these systems is that they all employ relatively large rigid bodies so that for the implantation a relatively large incision through the endothelium of the cornea is necessary. This surgical intervention leads not only to damage and loss of part of the unregeneratable cornea endothelial cells; in addition, with the size of the incision the danger of formation of a corneal edema increases, as does that of astigmatism arising. Another disadvantage is that each IOL must be adapted separately to the specific requirements and it is consequently necessary to produce and store a great number of types having different thicknesses.

EP-A-0308130 discloses deformable resilient intraocular lenses which are made from a mixture of monofunctional acrylic or methacrylic acid esters with addition of small amounts of difunctional acrylic of methacrylic acid esters. The production of the lenses is carried out in a conventional manner outside the body and as a result adjusting the lens thickness and the refraction values is not possible during the operation.

DE-C-3702625 discloses intraocular lenses for implantation after an extracapsular cataract which consists of an elastic silicones shell which is provided with a transparent filling of curable material. The curable material is to consist of "transparent acryl" to which a photoinitiator is added. No particulars on the nature of the monomers or photoinitiators used are to be found in this patent specification.

It is an object of the present invention to provide a photopolymerizable mass which during the operation on the eye can either by directly introduced into the capsule bag or can be introduced into the eye into a previously implanted resilient envelope. Since via the injection point, after curing the material is in direct contact with the eye interior, it is essential that the intraocular-lens filling material be at the most negligibly toxic and for no appreciable amounts to be extractable out of the polymerized material.

This object, and other objects and advantages of the present invention, will appear more clearly from the following specification and examples.

SUMMARY OF THE INVENTION

The method of the present invention is characterized primarily by providing a photopolymerizable composition that contains the following components:

a) 90–99.99% by weight, preferably 94–99.799% by weight, of at least one at least difunctional acrylic and/or methacrylic acid ester, b) 0.01–5% by weight, preferably 0.1–2% by weight, of at least one photoinitiator which is activatable with light in the wavelength range 400–500 nm, c) 0–9.98% by weight, preferably 0.001–2% by weight, of a UV-absorber which can absorb light of wavelengths <400 nm, and d) 0–9.98% by weight, preferably 0.1–2% by weight, of other auxiliary substances, such as dyes or activators for the photoinitiator, for example tertiary amines, the quantity particulars referring in each case to the total mass.

The at least difunctional acrylic or methacrylic acid esters preferably have a molecular weight >310 and are preferably the diacrylic or dimethacrylic acid esters of at least difunctional polyhydroxy compounds with aliphatic and/or aromatic skeleton having at least six chain links, the skeleton consisting of the atoms carbon, oxygen, nitrogen.

Well-suited are for example the diacrylic or dimethacrylic acid esters of bisphenols, for example bisphenol A or the bishydroxypolyalkoxy bisphenol A derivatives lengthened with ethylene oxide or proplyene oxide. Preferred here are the bisphenol A types lengthened on both sides with 1 to 5 and in particular 1–3 ethylene oxide units. Particularly preferred are compounds of the formula I.

Formula I:

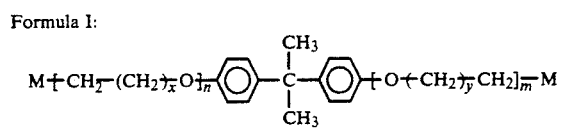

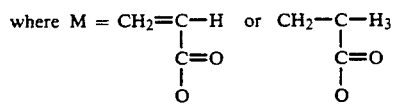

and n, m = 1–5, in particular 1–3, and x, y = 1, 2, 3, in particular 1.

Also well-suited are the bisacrylic acid or bismethacrylic acid esters of cycloaliphatic diols, in particular the cyloaliphatic diols lengthened with ethylene oxide and propylene oxide. Particularly suitable are the diols of the bis-(hydroxymethyl)-tricyclo[5.2.1.0$^{2.6}$]decane lengthened with ethylene oxide. Preferably, each OH group is lengthened with 1–5 and in particular with 1–3 ethylene oxide units.

Well-suited at least difunctional acrylic acid or methacrylic acid esters are also the reaction products of at least two parts hydroxyalkyl acrylate of hydroxyalkyl methacrylate with at least difunctional polyisocyanates having an aliphatic or aromatic skeleton. Particularly preferred are the reaction products of 2 parts hydroxyalkyl methacrylates, for example hydroxy proplymethacrylate, with 1 part trimethyl hexamethylene diisocyanate.

For setting the flow properties, viscosity, and optical properties it is possible to mix various at least difunctional acrylic acid or methacrylic acid esters together.

It is possible to use as component b) photoinitiators which absorb light in the range 400-500 nm, such as alpha-diketones, as known from DE-A-2302820 and DE-A-2251045, in particular camphor quinone, benzil and phenanthrene quinone, and mono and bisacylphosphine oxides as are known from EP-A-0184094 and EP-A-73413, EP-A-7508 and EP-A-57474; particularly preferred are for example 2,4,6-trimethylbenzoyldiphenylophosphine oxide and bis-(2,6-dichlorobenzoyl)-4-n-propylphenylphosphine oxide or bis-(2,6-dichlorobenzoyl)-4-n-butylphenylphosphine oxide.

To accelerate the polymerization and reduce the smear layer and the remaining monomers it may be expedient to use so-called activators together with the photoinitiators. Particularly suitable for this purpose are tertiary amines such as trihexyl amine, triethyl amine, triethanol amine and the like. Particularly well-suited are also the polyhydroxyalkyl amines reacted with methacrylic or acrylic acid ester.

To protect the retina from instant UV radiation it may be expedient to provide the photopolymerizable compositions with so-called UV absorbers. Particularly well-suited are UV absorbers which ensure as completely as possible absorption of the wavelength range 400 nm without filtering out the wavelength >400 nm necessary for the polymerization. Well-suited are for example benzophenones containing substituents such as hydroxyl and/or alkoxyl groups in 2 and/or 4 position, and furthermore substituted benzotriazoles and acrylates phenyl-substituted in 3 position, possibly with cyano groups in 2 position and salicylates. Well-suited in particular are the UV absorbers containing groups which are incorporated in the molecule and can be polymerized in, such as acrylic acid or methacrylic acid esters.

It may further be expedient for adjusting the viscosity or the refractive index to use organic and/or inorganic fillers. Inorganic fillers are for example pyrogenic silicon dioxide which has preferably been surface-treated with silanes. It should however be ensured when using inorganic fillers that the refractive index matches the other components to avoid any opacifying of the lens occurring For setting a certain thixotropy it is possible to use 0.5-3% by weight silanized pyrogenic silica Organic fillers may for example be polymeric fillers which may be soluble or insoluble in the monomers used. With insoluble polymers the refractive index of the polymer should match that of the monomers after the polymerization close enough to avoid any opacifying of the polymerized lens occurring. Soluble polymers may for example be polymethylmethacrylate or the like. They serve to adjust the viscosity or the refractive index of the polymer.

If the intraocular-lens filling material is to be filled into a previously implanted thin pliable elastic plastic envelope, then the refractive index of the polymerized intraocular-lens filling material and the plastic envelope should also be matched as far as possible to avoid causing any refraction phenomena at the envelope/filling interface.

The preparation of the intraocular-lens filling material is carried out in that the monomers to be used are stirred with the initiators and possibly added activators, UV absorbers and/or fillers, until a homogeneous clear mixture is formed. This mixture can then be introduced into the administering vessels; it is particularly advantageous to carry out a sterile filtration before the filling. It is however also possible to carry out a sterilization after filling for example by thermal treatment.

When using the intraocular-lens filling materials according to the invention the attending physician advantageously adopts the following procedure.

After opening the phacocyst by discission the anterior chamber is opened by a narrow lance incision at the upper or temporal side of the edge of the cornea. The lens mass is expressed, scooped out or frozen out by means of a cryoord or with a flushing suction syringe. A method permitting removal of the lens through a very small incision is phacoemulsification (F. Hollwich, Augenheilkunde, Thieme Verlag, Stuttgart 1979, p. 133-137). The lens can be removed intracapsulary, i.e. together with the phacocyst, or extracapsulary.

In the case of an intracapsular cataract extraction the capsule must be replaced by a thin pliable resilient plastic shell (e.g. silicone) into which the intraocular-lens filling material is introduced. In the case of the extracapsulary extraction the practically intact capsule bag can play the part of the silicone envelope. This method does not however exclude the additional use of the plastic envelope. The subsequent hardening of the filling material is then done with the aid of light in the wavelength range 400-500 nm by exposing through the dilated pupil.

The advantages obtained when using the intraocular filling materials according to the invention are thus:
minimum possible damage to the natural eye,
making of the individual lens during the operation,
setting of the refraction values during the operation,
low toxicity,
good retention in the capsule or plastic envelope by low shrinkage and
low content of residual monomers and extractable substances.

Hereinafter the invention will be explained in detail with the aid of examples.

EXAMPLES 1-7

Intraocular filling materials are made by mixing the monomers indicated in Table I with the contents (% by weight) given in the Table of initiators, activators and UV absorbers. Agitation is continued under slight heating until a clear solution is formed. The through-polymerized layer thickness is determined by introduction into a plastic cylinder ($\phi 8$ mm, h 20 mm) and 20 sec. irradiation with a dental irradiating unit (Elipar 2, Espe Company, wavelength range 400-500 nm). The determination of the smear layer is carried out by introducing the material into a cylinder of plastic ($\phi 15$ mm, h 1.5 mm) and likewise 20 sec. irradiation with Elipar 2. Thereafter the disc is weighed, whereupon the smear layer is removed from the surface with an isopropanol moist cloth, blown dry with compressed air and weighed again.

For determining the residual monomers, between two slides specimens for the smear layer determination as described above are made They are ground to a powder with a grain size <200 $\mu$m. From the powder a 10% methylene chloride solution is prepared which is treated for 3-5 min. in an ultrasonic bath, centrifuged and possibly filtered. The evaluation is via the external standard method using HPLC

| No. | Monomer | UV absorber (% by weight) | Initiators (% by weight) | Activators (% by weight) | Layer Thickness (mm) | Residual monomer | Smear Layer (mg/cm$^2$) |
| --- | --- | --- | --- | --- | --- | --- | --- |
| 1 | bis-(acryloyl-oxyethyl-oxymethyl)-tricyclo-[5.2.1.0$^{0.6}$] decane | — | 2,4,6-trimethyl-benzoyl-diphenyl phosphine oxide (0.5%) | — | 7 | 0.5 | 0.3 |
| 2 | bis-(acryloyl-oxyethyl-oxyethyl-oxymethyl)-tricyclo-[5.2.1.0$^{0.6}$] decane | 2-hydroxy-4-methoxy-benzophenone (0.1%) | bis-(2,6 dichloro-benzoyl)-4-n-propyl-phenylphosphine oxide (0.5%) | — | 12.5 | 0.2 | 0.3 |
| 3 | 2,2-bis [4-(acryloyl-oxyethyl-oxy)phenyl] propane | — | camphor quinone (0.22%) + 2,4,6-trimethyl-benzoyl-diphenylphosphine oxide (0.5%) | methyl diethanol amine (1%) | 11 | 0.2 | 2 |
| 4 | 2,2-bis [4-(acryloyl-oxyethyl-oxyethyloxy) phenyl] propane | — | bis (2,6 dichloro-benzoyl)-4-n-pro-phylphenylphosphine oxide (0.5%) | — | 7 | 0.4 | 2 |
| 5 | 2,2-bis [4-(acryloyl-oxyethyl-oxyethyloxy) phenyl]-propane | 2-hydroxy-4-methoxy-banzophenone (0.1%) | bis (2,6) dichloro-benzoyl)-4-n-pro-pylphenylphosphite oxide (0.5%) | — | 9 | 0.4 | 2 |
| 6 | 2,2-bis [4-methacry-loyl-oxyethyl-oxy-ethyl-oxy)phenyl] propane | — | bis (2,6 dichloro-benzoyl)-4-n-butyl-phenylphosphine oxide (0.5%) | — | 7.2 | 0.4 | 4 |
| 7 | 2,2-bis [methacry-loyl-oxyethyl-oxy-ethyl-oxy)phenyl] propane | 2-hydroxy-4-methoxy-benzo-phenone (0.1%) | bis (2,6 dichloro-benzoyl)-4-n-propyl-phenylphosphine oxide (0.5%) | — | 7.0 | 0.6 | 5 |

Silicone envelopes or shells as can be employed for pliable intraocular lenses can be filled very satisfactorily with all these compositions; the smear layer was so slight that the hardened filling could not be removed without destroying the shell; when using monofunctional acrylic or methacrylic acid esters the smear layer is so large that no stable filling can be produced in the intraocular lens.

With the mixtures of examples 4, 5, 6 and 7 cytotoxical investigations were carried out by curing the filling materials between two slides (20 sec. irradiation with Elipar 2). The polymer discs thus made were fixed under sterile conditions with a non-cytotoxic TCAB (Tissue culture adhesive system for biomaterials) and introduced into slide culture flasks. The preparations were then grown with bovine endothelial cells and epithelial cells in the presence of $^3$H TdR. The incubation time was 24 h. In the evaluation, the cytoplasma propagation, the absence of nuclei and the crosslinking of the cells were observed It was found in all specimens that 95% of the nucleic and cytoplasmic structures had been preserved and only a slight crosslinking of the cells was to be observed. The materials are thus to be considered only slightly toxic. Thereafter, the unpolymerized monomer of example 7 was investigated for cytotoxicity. The same picture was obtained and the unpolymerized monomer also showed only moderately toxic properties.

The intraocular-lens filling materials according to the invention are thus very well-suited to the intended purpose because firstly they exhibit only a slight oxygen inhibition in the polymerization and secondly have only small contents of residual monomer and are to be classified as only moderately toxic.

The present invention is, of course, in no way restricted to the specific disclosure of the specification and Examples, but also encompasses any modification within the scope of the appended claims.

What we claim is:

1. A method of providing a composition for an eye, including the steps of:
   providing a photopolymerizable composition for preparing an intraocular-lens filling material, said composition containing the following components: a) 94-99.799% by weight of at least one of the group consisting of at least difunctional acrylic and methacrylic acid esters of at least difunctional polyhydroxy compounds having an aliphatic or aromatic skeleton with at least six chain links, the skeleton consisting of the atoms carbon and oxygen, b) 0.1-2% by weight of at least one photoinitiator that is activatable with light in the wavelength range 400-500 nm, c) 0.001-2% by weight of an UV-absorber that can absorb light of wavelengths <400 nm, and d) 0.1-2% by weight of other auxiliary substances, whereby in each case the quantity refers to the total mass;
   during an operation, introducing said photopolymerizable composition directly into an eye; and
   curing said photopolymerizable composition with light in the wavelength range 400-500 nm.

2. A method according to claim 1, in which said component d) auxiliary substances are selected from the group consisting of dyes and activators for said photoinitiator.

3. A method according to claim 2, in which said activator is a tertiary amine.

4. A method according to claim 1, which includes the step of using as said component a) difunctional acrylic or methacrylic acid esters having a molecular weight of greater than 310.

5. A method according to claim 1, in which as said component b) at least one of the group consisting of alpha-diketones and mono and bisacylphosphine oxides is used.

6. A method according to claim 1, in which said introducing step comprises introducing said photopolymerizable composition into a capsule bag of an eye.

7. A method according to claim 1, which includes the step of first implanting an artificial intraocular lens shell, and in which said introducing step comprises introducing said photopolymerizable composition into said lens shell.

8. A method of providing a composition for an eye, including the steps of:
providing a photopolymerizable composition for preparing an intraocular-lens filling material, said composition containing the following components:
a) 90-99.99% by weight of at least one of the group consisting of at least diacrylic and dimethacrylic acid esters of bisphenols, b) 0.01-5% by weight of at least one photoinitiator that is activatable with light in the wavelength range 400-500 nm, c) 0-9.98% by weight of an UV-absorber that can absorb light of wavelengths <400 nm, and d) 0-9.98% by weight of other auxiliary substances, whereby in each case the quantity refers to the total mass;
during an operation, introducing said photopolymerizable composition directly into an eye; and
curing said photopolymerizable composition with light in the wavelength range 400-500 nm.

9. A method according to claim 9, in which as said component a) the diacrylic or dimethacrylic acid esters of bisphenol A or the bishydroxypolyalkoxy bisphenol A derivatives lengthened with ethylene oxide or propylene oxide are used.

10. A method according to claim 10, in which as said component a) a compound of the general formula I is used:

Formula I:

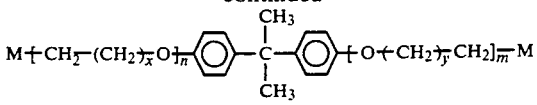

-continued

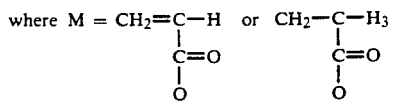

and n, m=1-5, in particular 1-3, and x, y=1, 2, 3, in particular 1.

11. A method according to claim 9, which includes 94-99.799% by weight of component a), 0.1-2% by weight of component b), 0.001-2% by weight of component c), and 0.1-2% by weight of component d).

12. A method of providing a composition for an eye, including the steps of:
providing a photopolymerizable composition for preparing an intraocular-lens filling material, said composition containing the following components:
a) 90-99.99% by weight of at least one of the group consisting of at least bisacrylic acid and bismethacrylic acid esters of cycloaliphatic diols or the corresponding derivatives in which the hydroxyl groups are lengthened with 1-5 and in particular 1-3 ethylene oxide or propylene oxide units, b) 0.01-5% by weight of at least one photoinitiator that is activatable with light in the wavelength range 400-500 nm, c) 0-9.98% by weight of an UV-absorber that can absorb light of wavelengths <400 nm, and d) 0-9.98% by weight of other auxiliary substances, whereby in each case the quantity refers to the total mass;
during an operation, introducing said photopolymerizable composition directly into an eye; and
curing said photopolymerizable composition with light in the wavelength range 400-500 nm.

13. A method according to claim 12, in which as said component a) the diols of the bis-(hydroxymethyl)-tricyclo-[5.2.1.0$^{2.6}$] decane lengthened with ethylene oxide are used, each hydroxyl group being lengthened with 1-5 and preferably with 1-3 ethylene oxide units.

* * * * *